United States Patent
Cowley

(10) Patent No.: US 11,298,106 B2
(45) Date of Patent: Apr. 12, 2022

(54) MINIMALLY-INVASIVE SURGICAL INSTRUMENT INCLUDING THREE-DIMENSIONAL (3D) ULTRASOUND IMAGING AND FOCUSED ULTRASOUND TREATMENT CAPABILITIES

(71) Applicant: COVIDIEN LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 381 days.

(21) Appl. No.: 16/118,781

(22) Filed: Aug. 31, 2018

(65) Prior Publication Data
US 2020/0069323 A1   Mar. 5, 2020

(51) Int. Cl.
*A61B 17/00* (2006.01)
*A61B 17/32* (2006.01)
(Continued)

(52) U.S. Cl.
CPC ............ *A61B 8/44* (2013.01); *A61B 8/085* (2013.01); *A61B 8/4477* (2013.01); *A61B 8/4494* (2013.01); *A61B 8/466* (2013.01); *A61B 8/483* (2013.01); *A61B 8/52* (2013.01); *A61B 17/00234* (2013.01); *A61B 17/320068* (2013.01); *A61B 90/37* (2016.02); *A61N 7/00* (2013.01); *A61N 7/02* (2013.01); *A61N 7/022* (2013.01); *G01S 7/52085* (2013.01); *A61B 17/00* (2013.01); *A61B 90/36* (2016.02); *A61B 2017/00022* (2013.01); *A61B 2017/00106* (2013.01); *A61B 2017/320069* (2017.08); *A61B 2017/320071* (2017.08); *A61B 2034/2063* (2016.02); *A61B 2090/367* (2016.02);
(Continued)

(58) Field of Classification Search
CPC ..... A61B 8/00; A61B 90/37; A61B 2090/378; A61B 2034/2063; A61B 17/00; A61B 17/320068; A61B 17/00234; A61B 2017/00022; A61B 2017/320069; A61B 2017/320071; A61B 2917/00106; A61B 90/06; A61B 90/36; A61B 2090/367; A61B 2090/3784; A61N 7/00; A61N 7/02; A61N 7/022; A61N 2007/0052; A61N 2007/0078; G01S 7/52085; G01S 15/8906
See application file for complete search history.

(56) References Cited

U.S. PATENT DOCUMENTS 5,181,514 A * 1/1993 Solomon .................. A61B 8/12
600/152
5,413,107 A    5/1995 Oakley et al.
(Continued)

*Primary Examiner* — Christopher L Cook
*Assistant Examiner* — Remy C Cooper
(74) *Attorney, Agent, or Firm* — Carter, DeLuca & Farrell LLP

(57) ABSTRACT

A surgical system includes a surgical instrument having a shaft and an end effector extending distally from the shaft. The end effector includes a plurality of ultrasound sensors supported about a support ring. The ultrasonic sensors are rotatable between an imaging orientation, wherein, the ultrasound sensors are directed in generally parallel orientations relative to one another for imaging tissue in an imaging mode, and at least one treatment orientation, wherein the ultrasound sensors are directed towards a common focus point for treating tissue in a treatment mode.

13 Claims, 3 Drawing Sheets

(51) Int. Cl.
*A61B 90/00* (2016.01)
*A61B 8/00* (2006.01)
*A61N 7/02* (2006.01)
*A61B 8/08* (2006.01)
*A61N 7/00* (2006.01)
*G01S 7/52* (2006.01)
*A61B 34/20* (2016.01)
*G01S 15/89* (2006.01)

(52) U.S. Cl.
CPC . *A61B 2090/378* (2016.02); *A61B 2090/3784* (2016.02); *A61N 2007/0052* (2013.01); *A61N 2007/0078* (2013.01); *G01S 15/8906* (2013.01)

(56) References Cited

U.S. PATENT DOCUMENTS

| | | |
|---|---|---|
| 5,465,724 A * | 11/1995 | Sliwa, Jr ............... A61B 8/12 |
| | | 600/459 |
| 5,471,988 A * | 12/1995 | Fujio ............... A61B 18/1492 |
| | | 600/439 |
| 6,626,855 B1 | 9/2003 | Weng et al. |
| 6,692,450 B1 | 2/2004 | Coleman |
| 6,719,694 B2 | 4/2004 | Weng et al. |
| 7,615,015 B2 | 11/2009 | Coleman |
| 8,152,721 B2 | 4/2012 | Michaeli et al. |
| 8,480,585 B2 | 7/2013 | Slayton et al. |
| 9,220,478 B2 | 12/2015 | Smith et al. |
| 9,986,916 B2 * | 6/2018 | Kohler ............... A61B 8/0841 |
| 2004/0158153 A1 | 8/2004 | Hirt et al. |
| 2006/0058678 A1 * | 3/2006 | Vitek ............... A61N 7/02 |
| | | 600/459 |
| 2007/0073135 A1 | 3/2007 | Lee et al. |
| 2009/0076390 A1 | 3/2009 | Lee et al. |
| 2012/0302877 A1 | 11/2012 | Harks et al. |
| 2014/0133269 A1 | 5/2014 | Hansen |
| 2014/0276079 A1 * | 9/2014 | Yamagata ............... A61B 8/445 |
| | | 600/459 |
| 2015/0257779 A1 | 9/2015 | Sinelnikov et al. |
| 2016/0338675 A1 * | 11/2016 | Kubota ............... A61B 90/11 |
| 2017/0245875 A1 * | 8/2017 | Timm ............... A61B 17/29 |
| 2019/0053781 A1 * | 2/2019 | Stigall ............... A61B 8/4461 |
| | | 600/445 |

* cited by examiner

MINIMALLY-INVASIVE SURGICAL INSTRUMENT INCLUDING THREE-DIMENSIONAL (3D) ULTRASOUND IMAGING AND FOCUSED ULTRASOUND TREATMENT CAPABILITIES

BACKGROUND

Technical Field

The present disclosure relates generally to minimally-invasive surgery. More specifically, the present disclosure relates to a minimally-invasive surgical instrument including three-dimensional (3D) ultrasound imaging capability to facilitate visualization of tissue structures within an internal surgical site, and focused ultrasound tissue treatment capability to facilitate treatment of target tissue with the internal surgical site, e.g., after locating the target tissue using the imaging capability.

Background of Related Art

Liver tumors are relatively common occurrences and, as a result, surgical procedures involving the treatment or removal of liver tumors are also relatively common. Despite being relatively common, minimally-invasive surgical procedures to treat or remove liver tumors remain difficult, particular with respect to accurately locating the liver tumor. As a result, larger-than-necessary tracts of liver tissue are treated (e.g., ablated) or removed (e.g., resected) to ensure that the entire tumor is treated or removed.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein.

Provided in accordance with aspects of the present disclosure is a surgical system including a surgical instrument having a shaft and an end effector extending distally from the shaft. The end effector includes a plurality of ultrasound sensors supported about a support ring. The ultrasonic sensors are rotatable between an imaging orientation, wherein the ultrasound sensors are directed in generally parallel orientations relative to one another for imaging tissue in an imaging mode, and at least one treatment orientation, wherein the ultrasound sensors are directed towards a common focus point for treating tissue in a treatment mode.

In an aspect of the present disclosure, in the imaging orientation, each ultrasound sensor of the plurality of ultrasound sensors is configured to emit an ultrasound wave, receive an echoed wave, and output the echoes wave to be reconstructed to produce a real-time 3D ultrasound video image.

In another aspect of the present disclosure, in the treatment orientation, the ultrasound sensors are configured to emit ultrasound waves towards the common focus point to ablate tissue at the common focus point.

In yet another aspect of the present disclosure, the end effector is configured to pivot relative to the shaft about at least one axis.

In still another aspect of the present disclosure, each ultrasound sensor is supported by an outer ring rotatably disposed about the support ring.

In still yet another aspect of the present disclosure, the surgical instrument further includes a housing. In such aspects, the shaft extends distally from the housing.

In another aspect of the present disclosure, the housing supports a first activation button for selectively activating the plurality of ultrasound sensors in the imaging mode and a second activation button for selectively activating the plurality of ultrasonic sensors in the treatment mode.

In another aspect of the present disclosure, the shaft and the end effector are together rotatable relative to the housing.

In still another aspect of the present disclosure, the system further includes a control system configured to receive the echoed waves from the plurality of ultrasound sensors and reconstruct the echoed waves to produce a real-time 3D ultrasound video image.

In yet another aspect of the present disclosure, the control system further includes a visual display configured to display the real-time 3D ultrasound video image.

A method of surgery provided in accordance with aspects of the present disclosure includes inserting an end effector of a surgical instrument into an internal surgical site; activating, in an imaging mode, a plurality of ultrasound sensors of the end effector to produce a real-time 3D ultrasound video image of the internal surgical site; viewing the real-time 3D ultrasound video image on a visual display to identify a target tissue; and activating, in a treatment mode, the plurality of ultrasound sensors of the end effector to ablate the target tissue.

In an aspect of the present disclosure, in the imaging mode, each ultrasound sensor of the plurality of ultrasound sensors is configured to emit an ultrasound wave, receive an echoed wave, and output the echoes wave to produce the real-time 3D ultrasound video image.

In another aspect of the present disclosure, in the treatment mode, the ultrasound sensors are configured to emit ultrasound waves towards a common focus point to ablate the target tissue.

In yet another aspect of the present disclosure, the method further includes rotating the plurality of ultrasound sensors to an imaging orientation before activating the plurality of ultrasound sensors in the imaging mode and/or rotating the plurality of ultrasound sensors to a treatment orientation before activating the plurality of ultrasound sensors in the treatment mode.

BRIEF DESCRIPTION OF THE DRAWINGS

Various aspects and features of the present disclosure are described herein with reference to the drawings, wherein like reference numerals identify similar or identical components, and.

DETAILED DESCRIPTION

Figure 1:
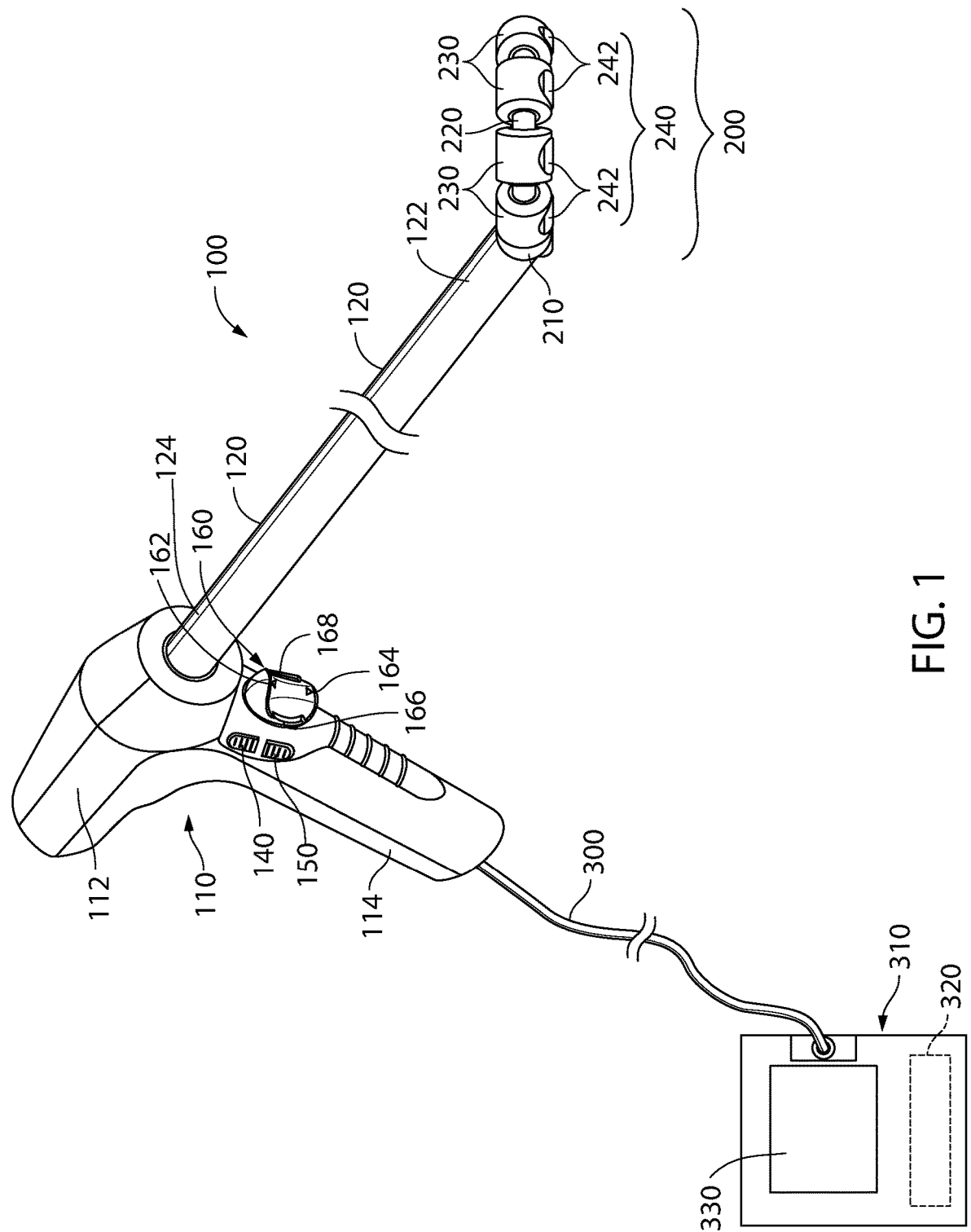
FIG. 1 is a top, front, perspective view of a surgical instrument provided in accordance with aspects of the present disclosure.

Turning to FIG. 1, provided in accordance with the present disclosure is a minimally-invasive surgical instrument including three-dimensional (3D) ultrasound imaging capability to facilitate performing a surgical procedure such as, for example, by facilitating visualization of tissue structures within an internal surgical site. The surgical instrument further includes focused ultrasound tissue treatment capability to facilitate performing a surgical procedure such as, for example, by enabling treatment, e.g., ablation, of tissue structures within an internal surgical site after accurately locating such tissue structures utilizing the imaging capability. The surgical instrument, generally identified by reference numeral 100, is detailed herein for use in connection with hepatic surgical procedures performed on the liver; however, the aspects and features of the present disclosure are equally applicable for use in other surgical procedures and/or with respect to other tissue structures.

Continuing with reference to FIG. 1, surgical instrument 100 generally includes a housing 110, a shaft 120 extending distally from housing 110, and an end effector 200 extending distally from a distal end portion 122 of shaft 120. Surgical instrument 100 is further configured, in embodiments, to enable pivoting of end effector 200 relative to shaft 120, as detailed below, thus facilitating the insertion of surgical instrument 100 through a minimally-invasive access port (not shown), e.g., a trocar, and/or manipulation of end effector 200 within a minimally-invasive surgical site.

Housing 110 of surgical instrument 100 defines a pistol-grip configuration (although other configurations are also contemplated) including a barrel portion 112 and a fixed handle portion 114 depending from barrel portion 112. Shaft 120 extends distally from barrel portion 112, while fixed handle portion 114 is ergonomically configured to facilitate a user gripping and manipulating housing 110. A cable 300 couples housing 110 to a control system 310. Control system 310 provides power to surgical instrument 100, although power may alternatively be provided by a battery (not shown) internal to housing 110 or via a separate cable (not shown) connected directly to a mains power supply (not shown). Control system 310 also includes an image processing unit 320 and a visual display 330. Although illustrated as incorporated into a single enclosure, control system 310 may include separate components connected to one another such as, for example, a computer for image processing and a video monitor connected to the computer for visual display. In other embodiments, imaging processing and/or image display may be provided on or within housing 110. Additionally or alternatively, wireless communication to local or remote components, e.g., a computer and/or display, may be provided instead of a wired connection using cable 300.

Housing 110 of surgical instrument 100 further includes a plurality of actuators 140-160 such as, for example, an ON/OFF imaging button 140, an ON/OFF tissue treatment button 150, and an articulation joystick 160 including first and second pivoting buttons 162, 164, respectively, and first and second rotation buttons 166, 168, respectively. ON/OFF imaging button 140 enables selective activation and deactivation of 3D ultrasound imaging by end effector 200; ON/OFF tissue treatment button 150 enables selective activation and deactivation of focused ultrasound tissue treatment by end effector 200; and articulation joystick 160 enables pitch articulation, e.g., pivoting, of end effector 200 relative to shaft 120 and roll articulation, e.g., rotation, of end effector 200 and shaft 120 relative to housing 110. However, in embodiments, end effector 200 may be configured to rotate relative to shaft 120 and housing 110, or rotation may be eliminated entirely. Likewise, in embodiments, pivoting of end effector 200 relative to shaft 120 may be eliminated.

Articulation joystick 160 communicates with a powered articulation mechanism (not shown) including one or more motors operably coupled with proximal end portion 124 of shaft 120 to enable rotation of shaft 124 relative to housing 110 in the corresponding direction according to the button actuated, e.g., rotation button 166 or rotation button 168. The powered articulation mechanism also includes one or more motors operably coupled with end effector 200 via one or more translation drives, rotation drives, cables, linkages, tilt plates, etc. to enable articulation of end effector 200 relative to shaft 120 in the corresponding direction according to the button actuated, e.g., pivoting button 162 or pivoting button 164. As an alternative to a powered articulation mechanism, a manual articulation mechanism including, for example, one or more manually-actuated rotation knobs (not shown) and/or articulation wheels (not shown), may be provided. In either configuration, end effector 200 is articulatable relative to housing 110 about two axes (a pitch axis and a roll axis), although in some embodiments articulation about three axes (further incorporating yaw axis articulation) or only a single axis may be provided.

Figure 2:
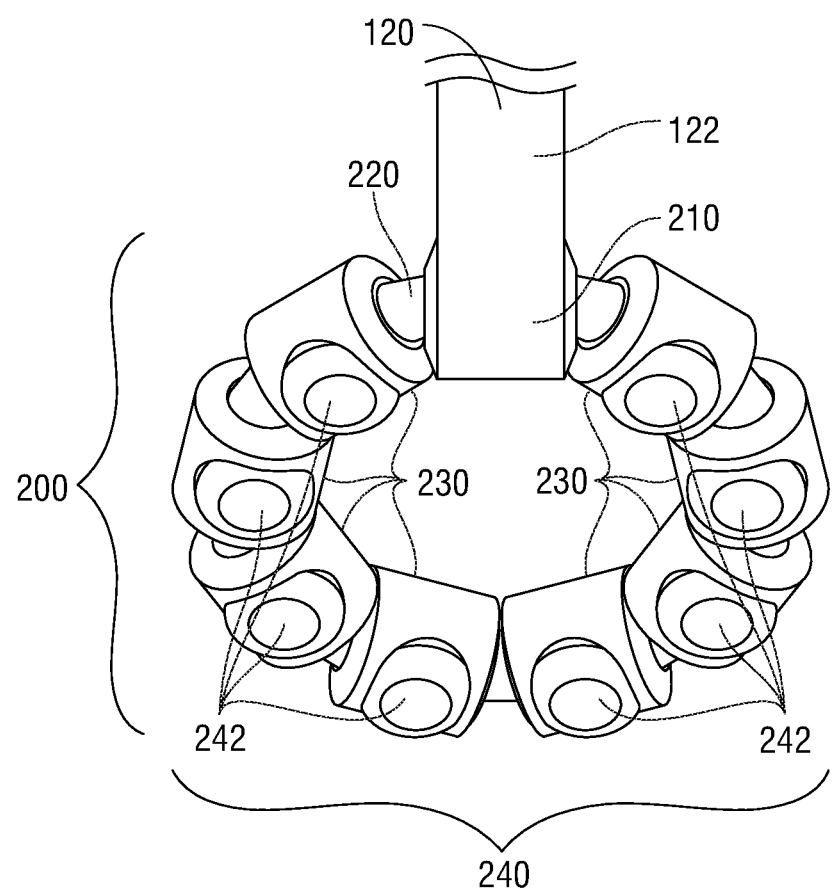
FIG. 2 is a bottom, front, perspective view of an end effector of the surgical instrument of FIG. 1.

Referring also to FIG. 2, as noted above, shaft 120 extends distally from housing 110 and end effector 200 extends distally from distal end portion 122 of shaft 120. A proximal end portion 124 of shaft 120, more specifically, is coupled to powered articulation mechanism 180, e.g., to enable rotation of shaft 120 and, thus, end effector 200 relative to housing 110, at or within housing 110. Shaft 120 extends distally from proximal end portion 124 to distal end portion 122. Distal end portion 122 is operably coupled with end effector 200.

End effector 200 includes a pivot sleeve 210, an inner support ring 220, and a plurality of outer rings 230. Pivot sleeve 210 is fixedly engaged with distal end portion 122 of shaft 120 and is disposed about a portion of inner support ring 220 to support inner support ring 220 at distal end portion 122 of shaft 120 and to permit pivoting, e.g., pitch articulation, of inner support ring 220 relative to pivot sleeve 210 and, thus, relative to shaft 120. This pivoting of end effector 200 relative to shaft 120 is controlled, for example, via selective actuation of pivoting buttons 162, 164 of articulation joystick 160 (see FIG. 1). The fixed engagement of pivot sleeve 210 of end effector 200 with distal end portion 122 of shaft 120 also transmits rotation of shaft 120 relative to housing 110, e.g., imparted via actuation of rotation buttons 166, 168 of articulation joystick 160 (see FIG. 1), to end effector 200 such that end effector 200 is rotated together with shaft 120 relative to housing 110.

Inner support ring 220 supports outer rings 230 thereon and, as noted above, is pivotable relative to pivot sleeve 210 and, thus, relative to shaft 120. Inner support ring 220 may define an arcuate configuration forming a circular or elliptical ring (as illustrated), may include a plurality of angled segments interconnected with one another to define a polygonal ring, or may define any other suitable geometric ring-shaped configuration. Further, in embodiments, the inner support ring 220 may be compressible or collapsible to assume a lower-profile configuration, e.g., wherein opposing sides of inner support ring 220 are approximated relative to one another to define an elongated oval aligned with the longitudinal axis of shaft 120, thus facilitating insertion through a minimally-invasive access port (not shown). In other embodiments, inner support ring 220 is a discontinuous ring capable of assuming a linear or other suitable configuration to facilitate insertion through a minimally-invasive access port (not shown) and thereafter returning to a circular or elliptical configuration, e.g., the circular configuration illustrated in FIG. 2.

Continuing with reference to FIGS. 1 and 2, each outer ring 230 supports an ultrasound sensor 242. The ultrasound sensors 242 cooperate to form an ultrasound sensor array 240. Ultrasound sensors 242 are arranged about the circumference of inner support ring 220 in spaced-apart relation relative to one another. In embodiments, one or more pairs of ultrasound sensor 242 diametrically oppose one another. Although eight (8) sensors are illustrated, greater or fewer ultrasound sensors 242 are also contemplated. In embodiments, an ultrasound sensor 242 is also disposed on pivot sleeve 210 and arranged similarly with the ultrasound sensors 242 of outer rings 230. Any suitable configuration where ultrasound sensors 242 are appropriately spaced about inner support ring 220 (whether inner support ring 220 defines a circular, elliptical, polygonal, or other suitable geometric-shaped configuration, etc.) to enable reconstruction of a 3D ultrasound image therefrom and to enable focus ultrasound tissue treatment may be provided.

Outer rings 230 are slidably fixed relative to inner support ring 220 but are rotatable relative to inner support ring 220. As such, ultrasound sensors 242 are likewise slidably fixed relative to inner support ring 220 but rotatable relative to inner support ring 220. Ultrasound sensors 242, more specifically, are rotatable, via the rotation of outer rings 230, between an imaging orientation and a treatment orientation.

In the imaging orientation, ultrasound sensors 242 define a substantially two-dimensional (2D) ultrasound sensor array 240 with ultrasound sensors 242 directed in generally parallel orientations relative to one another (wherein "substantially" and "generally" account for manufacturing, material, use, environmental, and other tolerances). As such, in the imaging orientation, upon activation of ultrasound sensors 242, e.g., via activation of the ON/OFF imaging button 140 (FIG. 1), each ultrasound sensor 242 in the ultrasound sensor array 240 is configured to emit ultrasound waves, e.g., high-frequency sound waves, and to receive echoed waves produced by the reflection of the ultrasound waves against the various tissue structures encountered. As detailed below, the echoed waves received by each ultrasound sensor 242 are output to control system 310 to enable reconstruction and display of a real-time 3D ultrasound video image.

To achieve the treatment orientation, outer rings 230 are rotated about and relative to inner ring 220 to thereby rotate ultrasound sensors 242 radially inwardly such that, rather than defining a substantially two-dimensional (2D) ultrasound sensor array 240 with ultrasound sensors 242 directed in generally parallel orientations relative to one another, as in the imaging orientation, ultrasound sensors 242 are directed towards a common focus point to concentrate the ultrasonic waves at the common focus point for treating tissue therewith, as detailed below. In embodiments, multiple treatment orientations may be provided where, in each treatment orientation, ultrasound sensors 242 are directed towards a different common focus point, thus enabling treatment of tissue at different depths, depending upon the treatment orientation utilized.

Referring still to FIGS. 1 and 2, rotation of outer rings 230 and, thus ultrasound sensors 242, between the imaging orientation and the treatment orientation may be effected automatically based upon the mode activated by a user. For example, if ultrasound sensors 242 are disposed in the imaging orientation and the ON/OFF tissue treatment button 150 is activated to initiate the treatment mode, ultrasound sensors 242 are first rotated to the treatment orientation before treatment is initiated. Similarly, if ultrasound sensors 242 are disposed in the treatment orientation and the ON/OFF imaging button 140 is activated, ultrasound sensors 242 are first rotated to the imaging orientation before imaging is initiated. Of course, if ultrasound sensors 242 are already in the appropriate orientation, no such rotation is required upon activation of the imaging or treatment mode.

Rotation of outer rings 230 to rotate ultrasound sensors 242 between the imaging and treatment orientations is effected, for example, via a powered drive mechanism (not shown) disposed within housing 110 and including one or more motors operably coupled outer rings 230 via one or more drives, cables, linkages, etc. to enable rotation of outer rings 230 about inner support ring 220, if necessary, according to the button actuated, e.g., ON/OFF imaging button 140 or ON/OFF tissue treatment button 150. In embodiments, outer rings 230 are biased towards one of the orientations, e.g., the imaging orientation. As an alternative to powered rotation, outer rings 230 may be rotated via a manual actuator (not shown) disposed on housing 110.

Figure 3A:
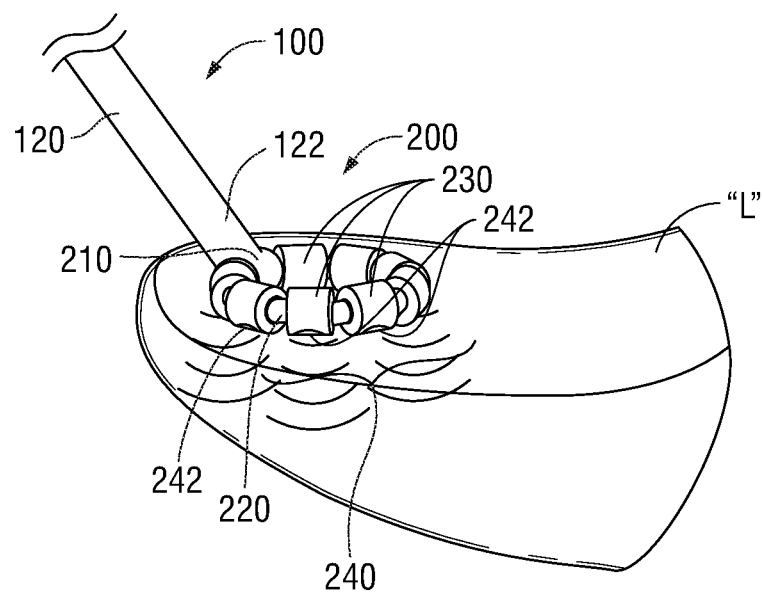
FIG. 3A is a side, perspective view illustrating a distal portion of the surgical instrument of FIG. 1 in use imaging liver tissue.
Figure 3B:
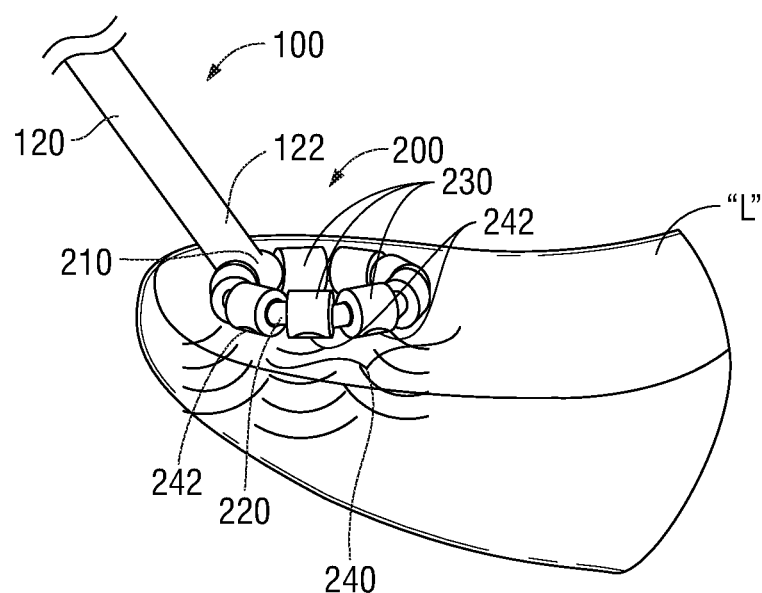
FIG. 3B is a side, perspective view illustrating the distal portion of the surgical instrument of FIG. 1 in use treating liver tissue.

Turning now to FIGS. 3A and 3B, surgical instrument 100 is illustrated in use in the imaging mode (FIG. 3A) and the treatment mode (FIG. 3B). With initial reference to FIG. 3A, in use, with respect to the liver "L," for example, end effector 200 is inserted through a minimally-invasive access port (not shown), e.g., a trocar, and is articulated, rotated, and/or otherwise maneuvered into position on the liver "L." 3D ultrasound imaging is then activated, e.g., by depressing ON/OFF imaging button 140 (FIG. 1).

With the imaging mode activated, and, thus, with ultrasound sensors 242 disposed in the imaging orientation, each ultrasound sensor 242 emits ultrasound waves and receives echoed waves produced by the reflection of the ultrasound waves against the various tissue structures encountered. The echoed waves received by each ultrasound sensor 242 are output to the image processing unit 320 (FIG. 1), e.g., by way of wires (not shown) extending through surgical instrument 100 and cable 300 (see FIG. 1). Image processing unit 320 (FIG. 1) utilizes the data from each of the ultrasound sensors 242 to reconstruct a 3D image. 3D image reconstruction may be provided via any suitable method including, for example, voxel-Based Methods (VBMs), Pixel-Based Methods (PBMs), or Function-Based Methods (FBMs). Other suitable methods for producing a 3D image from an ultrasound sensor array, e.g., ultrasound sensor array 240, are also contemplated.

The above-detailed process is repeated in real-time such that a stream of 3D images are produced, thus providing a real-time 3D ultrasound video image. The real-time 3D ultrasound video image is output to visual display 330 (FIG. 1), enabling a user to visualize the internal tissue structures, e.g., the liver "L," in real-time as end effector 200 is maneuvered within the internal surgical site with ultrasound sensors 242 activated in the imaging orientation.

Continuing with reference to FIG. 3A, in connection with FIGS. 1 and 2, end effector 200 is moved along the surface of the liver "L," thereby moving ultrasound sensor array 240 along the surface of the liver "L." The user may move ultrasound sensor array 240 in this manner while watching the real-time 3D ultrasound video image displayed on visual display 330. This enables the user to, for example, accurately locate a tumor to be treated.

Referring now to FIG. 3B, in connection with FIGS. 1 and 2, once the tumor is accurately located, the tumor may then be treated, e.g., ablated. In order to ablate the tumor, ultrasound sensors 242 are rotated to the treatment orientation and tissue treatment is initiated, e.g., in response to actuation of the ON/OFF tissue treatment button 150. With ultrasound sensors 242 activated in the treatment orientation, the ultrasound waves emitted from ultrasound sensors 242 are focused towards the common focus point and, thus are concentrated at the common focus point. This concentration of ultrasound waves at the common focus point serves to heat and ablate the tissue at the common focus point. The waves emitted by ultrasound sensors 242 in the imaging mode as compared to the treatment mode may be different in frequency, amplitude, wavelengths, etc., such that the waves emitted in each mode are turned for their particular purpose, e.g., imaging or treatment. Further, in embodiments, imaging and treatment may be performed simultaneously, e.g., with some ultrasound sensors 242 disposed in the imaging orientation and other ultrasound sensors 242 disposed in the treatment orientation, or in an alternating manner, to enable the user to both visualize and treat the tissue at the same time or in near time.

In the treatment mode, end effector 200 may be maneuvered to various positions and/or, in embodiments where multiple treatment orientations are provided, ultrasounds sensors 242 may be rotated to different treatment orientations, in order to ablate different portions of the tumor. Once ablation of the tumor is completed, confirmation can be obtained by returning to the imaging mode and viewing the liver "L" via the real-time 3D ultrasound video image displayed on visual display 330 (FIG. 1).

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system, comprising:
  a surgical instrument, including:
  a shaft; and
  an end effector extending distally from the shaft, the end effector including a pivot sleeve engaged with the shaft, the end effector including a plurality of ultrasound sensors supported about a support ring, the pivot sleeve arranged about a portion of the support ring to allow pivoting of the end effector with respect to the shaft, the ultrasonic sensors rotatable between an imaging orientation, wherein the ultrasound sensors are directed in parallel orientations relative to one another for imaging tissue in an imaging mode, and at least one treatment orientation, wherein the ultrasound sensors are directed towards a common focus point for treating tissue in a treatment mode,
  wherein each ultrasound sensor of the plurality of ultrasound sensors is supported by an outer ring of a plurality of outer rings rotatably disposed about the support ring, wherein each outer ring is rotatable relative to the support ring and relative to each other outer ring of the plurality of outer rings.

2. The surgical system according to claim 1, wherein, in the imaging orientation, each ultrasound sensor of the plurality of ultrasound sensors is configured to emit an ultrasound wave, receive an echoed wave, and output the echoes wave to be reconstructed to produce a real-time 3D ultrasound video image.

3. The surgical system according to claim 1, wherein, in the treatment orientation, the ultrasound sensors are configured to emit ultrasound waves towards the common focus point to ablate tissue at the common focus point.

4. The surgical system according to claim 1, wherein the surgical instrument further includes a housing, wherein the shaft extends distally from the housing.

5. The surgical system according to claim 4, wherein the housing supports a first activation button for selectively activating the plurality of ultrasound sensors in the imaging mode and a second activation button for selectively activating the plurality of ultrasonic sensors in the treatment mode.

6. The surgical system according to claim 4, wherein the shaft and the end effector are together rotatable relative to the housing.

7. The surgical system according to claim 1, further comprising:
  a control system configured to receive the echoed waves from the plurality of ultrasound sensors and reconstruct the echoed waves to produce a real-time 3D ultrasound video image.

8. The surgical system according to claim 7, wherein the control system further includes a visual display configured to display the real-time 3D ultrasound video image.

9. A method of surgery, comprising:
  inserting an end effector of a surgical instrument into an internal surgical site, the end effector including a plurality of ultrasound sensors supported about a support ring and a pivot sleeve arranged about a portion of the support ring, wherein each ultrasound sensor of the plurality of ultrasound sensors is supported by an outer ring of a plurality of outer rings rotatably disposed about the support ring;
  pivoting the end effector by rotating the support ring within the pivot sleeve;
  rotating the plurality of outer rings relative to one another to arrange the plurality of ultrasound sensors in an imaging orientation;
  activating, in an imaging mode, the plurality of ultrasound sensors of the end effector to produce a real-time 3D ultrasound video image of the internal surgical site;
  viewing the real-time 3D ultrasound video image on a visual display to identify a target tissue;
  rotating the plurality of outer rings relative to one another to arrange the plurality of ultrasound sensors in a treatment orientation; and
  activating, in a treatment mode, the plurality of ultrasound sensors of the end effector to ablate the target tissue.

10. The method according to claim 9, wherein in the imaging mode, each ultrasound sensor of the plurality of ultrasound sensors is configured to emit an ultrasound wave, receive an echoed wave, and output the echoes wave to produce the real-time 3D ultrasound video image.

11. The method according to claim 9, wherein, in the treatment mode, the ultrasound sensors are configured to emit ultrasound waves towards a common focus point to ablate the target tissue.

12. The method according to claim 9, further comprising at least one of:

rotating the plurality of ultrasound sensors to the imaging orientation before activating the plurality of ultrasound sensors in the imaging mode; or rotating the plurality of ultrasound sensors to the treatment orientation before activating the plurality of ultrasound sensors in the treatment mode.

13. The method according to claim 9, further comprising:

rotating the plurality of ultrasound sensors to the imaging orientation before activating the plurality of ultrasound sensors in the imaging mode; and rotating the plurality of ultrasound sensors to the treatment orientation before activating the plurality of ultrasound sensors in the treatment mode.

\* \* \* \* \*